United States Patent [19]
Capello et al.

[11] Patent Number: 5,702,477
[45] Date of Patent: Dec. 30, 1997

[54] ACETABULAR SHELL WITH SUPPLEMENTAL SUUPPORT AND METHOD

[75] Inventors: William N. Capello, Indianapolis, Ind.; Nicholas N. G. Dong, Little Falls, N.J.

[73] Assignee: Osteonics Corp., Allendale, N.J.

[21] Appl. No.: 647,404

[22] Filed: May 9, 1996

[51] Int. Cl.$^6$ .................................................. A61F 2/34
[52] U.S. Cl. .................................................. 623/22
[58] Field of Search .................................................. 623/22

[56] References Cited

U.S. PATENT DOCUMENTS

| | | |
|---|---|---|
| 2,947,308 | 8/1960 | Gorman. |
| 3,641,590 | 2/1972 | Michele. |
| 3,740,769 | 6/1973 | Haboush. |
| 3,896,504 | 7/1975 | Fischer. |
| 3,903,549 | 9/1975 | Deyerle. |
| 3,918,102 | 11/1975 | Eichler. |
| 4,245,360 | 1/1981 | Brinckmann et al.. |
| 4,792,337 | 12/1988 | Müller. |
| 4,883,489 | 11/1989 | Grundei et al.. |
| 4,883,490 | 11/1989 | Oh. |
| 4,904,265 | 2/1990 | Maccollum et al.. |
| 4,919,672 | 4/1990 | Millar et al. .............. 623/22 |
| 4,919,675 | 4/1990 | Dietschi. |
| 4,955,919 | 9/1990 | Pappas et al.. |
| 4,959,072 | 9/1990 | Morscher et al.. |
| 4,961,748 | 10/1990 | Frey et al.. |
| 5,108,447 | 4/1992 | Zeiler et al.. |
| 5,192,329 | 3/1993 | Christie et al.. |
| 5,226,917 | 7/1993 | Schryver. |
| 5,290,315 | 3/1994 | DeCarlo, Jr.. |
| 5,314,488 | 5/1994 | Hayashi et al.. |
| 5,314,490 | 5/1994 | Wagner et al.. |
| 5,326,367 | 7/1994 | Rabioneck. |
| 5,326,368 | 7/1994 | Collazo. |
| 5,370,703 | 12/1994 | Willert et al.. |
| 5,370,704 | 12/1994 | DeCarlo, Jr.. |
| 5,425,778 | 6/1995 | Zichner et al.. |

FOREIGN PATENT DOCUMENTS

| | | | |
|---|---|---|---|
| 2578162 | 9/1986 | France | 2/34 |

OTHER PUBLICATIONS

Waldemar Link GmbH & Co., "Partial Pelvis Replacement Endo–Model" 1993.
Landos Biomecanique, "Kar–Octopus" (date unknown).
A Natural–Implant, one page undated.

Primary Examiner—David Isabella
Assistant Examiner—John M. Black
Attorney, Agent, or Firm—Arthur Jacob

[57] ABSTRACT

An acetabular shell is implanted at an acetabulum in a deficient pelvis to establish an effective acetabular site with increased support in posterior and superior directions for an acetabular bearing insert to be affixed in place in the acetabular shell for the reception of a femoral head of a femoral component of a prosthetic hip implant, the acetabular shell including a domed portion having a convex outer surface for engaging the acetabulum, a concave inner surface for reception of the bearing insert, the inner surface extending along a spherical contour up to a generally hemispherical extent, and a rim between the outer and inner surfaces, the rim being placed adjacent an equatorial location along the domed portion and including a superior segment, an inferior segment longitudinally opposite the superior segment, a posterior segment and an anterior segment laterally opposite the posterior segment, an anchoring plate integral with the domed portion adjacent the superior segment of the rim, and a supplemental support web extending along the rim from the posterior segment to the plate at the superior segment, the support web projecting beyond the equatorial location for providing supplemental support for the bearing insert in the posterior and superior directions.

16 Claims, 3 Drawing Sheets

ACETABULAR SHELL WITH SUPPLEMENTAL SUUPPORT AND METHOD

The present invention relates generally to prosthetic hip implants and pertains, more specifically, to an acetabular shell for implant at an acetabulum in a more damaged or severely degenerated pelvis and to a method for providing supplemental support for a bearing insert placed at the implant site.

Where a pelvis is deficient at the acetabular site, perhaps as a result of excessive damage or severe degeneration through revision procedures, injury or disease, an acetabular shell of the type having an integral extended anchoring plate can be employed to provide an effective acetabular site for supporting an acetabular bearing insert of a prosthetic hip implant.

The present invention provides an acetabular shell of the type described, with increased effectiveness in managing the forces encountered in the replaced hip joint while enabling the accomplishment of the implant procedure with increased ease and accuracy. As such, the present invention attains several objects and advantages, some of which are summarized as follows: Provides an acetabular shell of the type described and having a supplemental support configuration enabling increased support against forces encountered in the hip joint, without an increase in complexity in either the manufacture or in the procedure for implant of the acetabular shell; enables conformance of the acetabular shell to conditions encountered at the implant site for providing maximum effectiveness concomitant with those conditions; is adapted readily to accommodate a wider variety of conditions encountered at the implant site; provides for a more accurate and secure affixation of an acetabular bearing insert under a wider variety of conditions encountered at an implant site; facilitates the implant procedure with increased effectiveness in providing supplemental support for a bearing insert placed at the implant site; provides a relatively simple construction readily manufactured of an effective biocompatible material for increased economy, while attaining increased reliability over an extended service life.

The above objects and advantages, as well as further objects and advantages, are attained by the present invention which may be described briefly as an acetabular shell for implant at an acetabulum in a deficient pelvis to establish an effective acetabular site with increased support in posterior and superior directions for an acetabular bearing insert to be affixed in place in the acetabular shell for the reception of a femoral head of a femoral component of a prosthetic hip implant, the acetabular shell comprising: a domed portion having a convex outer surface for engaging the natural acetabulum, a concave inner surface for reception of the bearing insert, the inner surface extending along a spherical contour up to a generally hemispherical extent, and a rim between the outer and inner surfaces, the rim being placed adjacent an equatorial location along the domed portion and including a superior segment, an inferior segment longitudinally opposite the superior segment, a posterior segment and an anterior segment laterally opposite the posterior segment; an anchoring plate integral with the domed portion adjacent the superior segment of the rim; and a supplemental support web extending along the rim from the posterior segment to the plate at the superior segment, the support web projecting beyond the equatorial location for providing supplemental support for the bearing insert in the posterior and superior directions.

In addition, the invention includes a method for providing increased support against posterior and superior forces exerted upon an acetabular bearing insert implanted at an acetabulum in a deficient pelvis for the reception of a femoral head of a femoral component of a prosthetic hip implant, the method comprising: placing an acetabular shell at the acetabulum of the pelvis, the acetabular shell including a domed portion having a convex outer surface for engaging the acetabulum, a concave inner surface for reception of the bearing insert, the inner surface extending along a spherical contour up to a generally hemispherical extent, and a rim between the outer and inner surfaces, the rim being placed adjacent an equatorial location along the domed portion and including a superior segment, an inferior segment longitudinally opposite the superior segment, a posterior segment and an anterior segment laterally opposite the posterior segment; securing the domed portion in the pelvis by anchoring an anchoring plate in the pelvis, the anchoring plate being integral with the domed portion adjacent the superior segment of the rim; and locating a supplemental support web of the domed portion for supplemental support of the bearing insert in the posterior and superior directions, the supplemental support web extending along the rim from the posterior segment to the plate at the superior segment and projecting beyond the equatorial location for providing the supplemental support for the bearing insert in the posterior and superior directions.

The invention will be understood more fully, while still further objects and advantages will become apparent, in the following detailed description of preferred embodiments of the invention illustrated in the accompanying drawing, in which.

Figure 1:
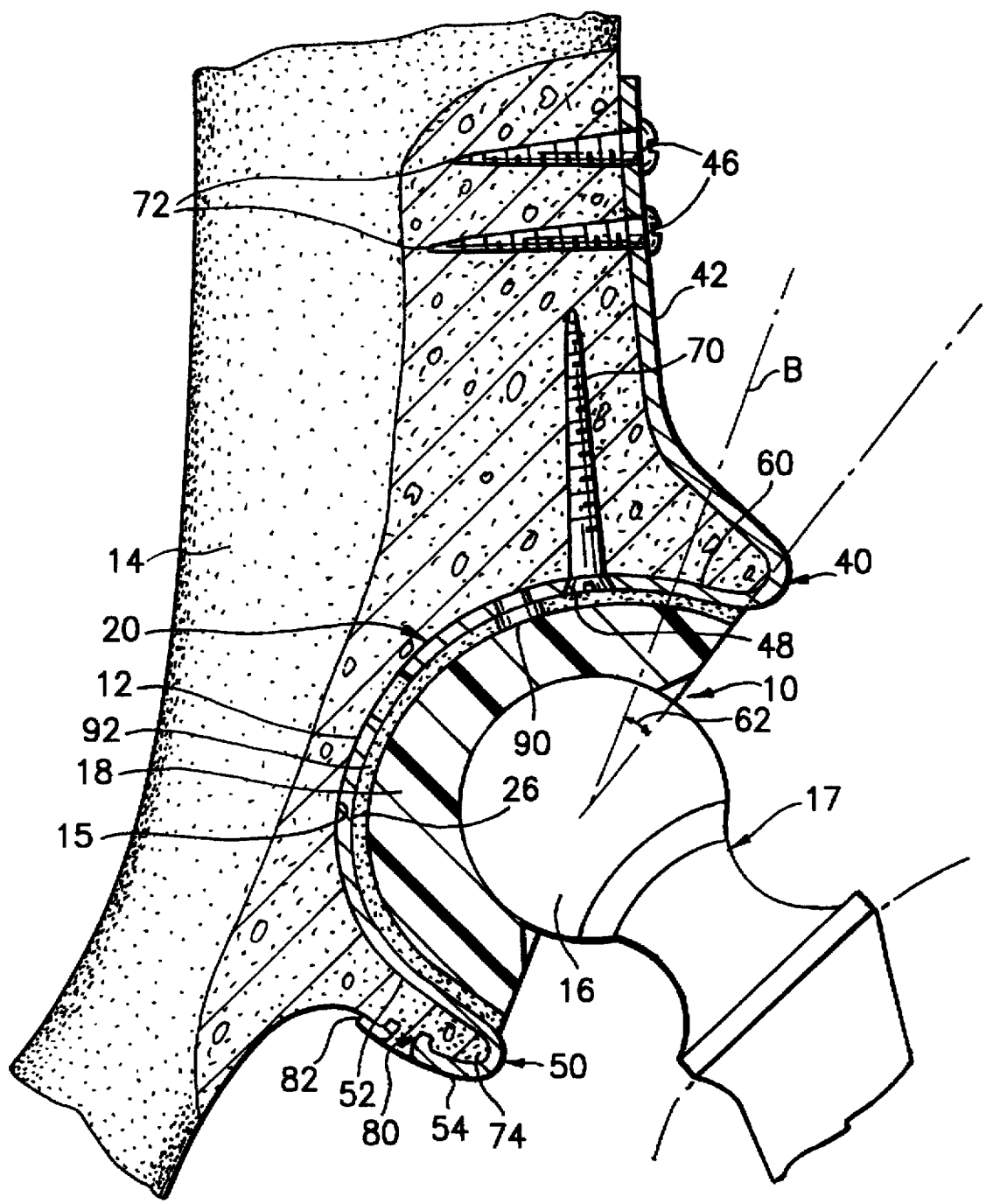
FIG. 1 is a somewhat diagrammatic longitudinal cross-sectional view showing a prosthetic hip implant with an acetabular cup assembly in place in a pelvis, utilizing an acetabular shell constructed in accordance with the present invention.

Referring now to the drawing, and especially to FIG. 1 thereof, a prosthetic hip implant 10 includes an acetabular cup assembly 12 implanted within a pelvis 14, placed within the acetabulum 15 of the pelvis 14, and cooperating with a femoral head 16 of a femoral component 17 seated within a bearing insert 18 of the acetabular cup assembly 12 in a now well known manner. The bearing insert 18 is affixed in place within an acetabular shell 20 constructed in accordance with the present invention. Acetabular shell 20 is affixed in place in the pelvis 14 and is constructed to provide supplemental support for the bearing insert 18 in posterior and superior directions in a manner which will be described fully below.

Figure 3:
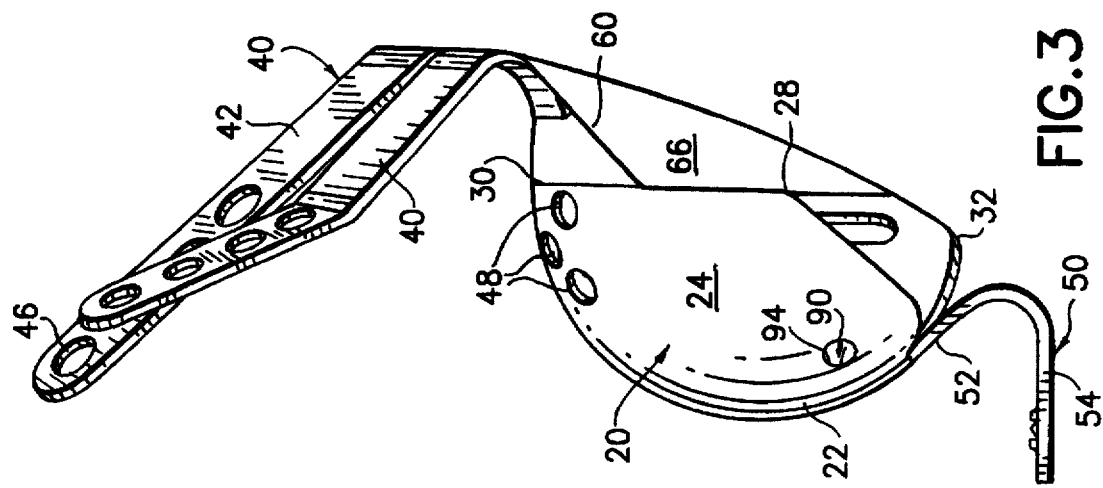
FIG. 3 is an elevational view of the acetabular shell.
Figure 2:
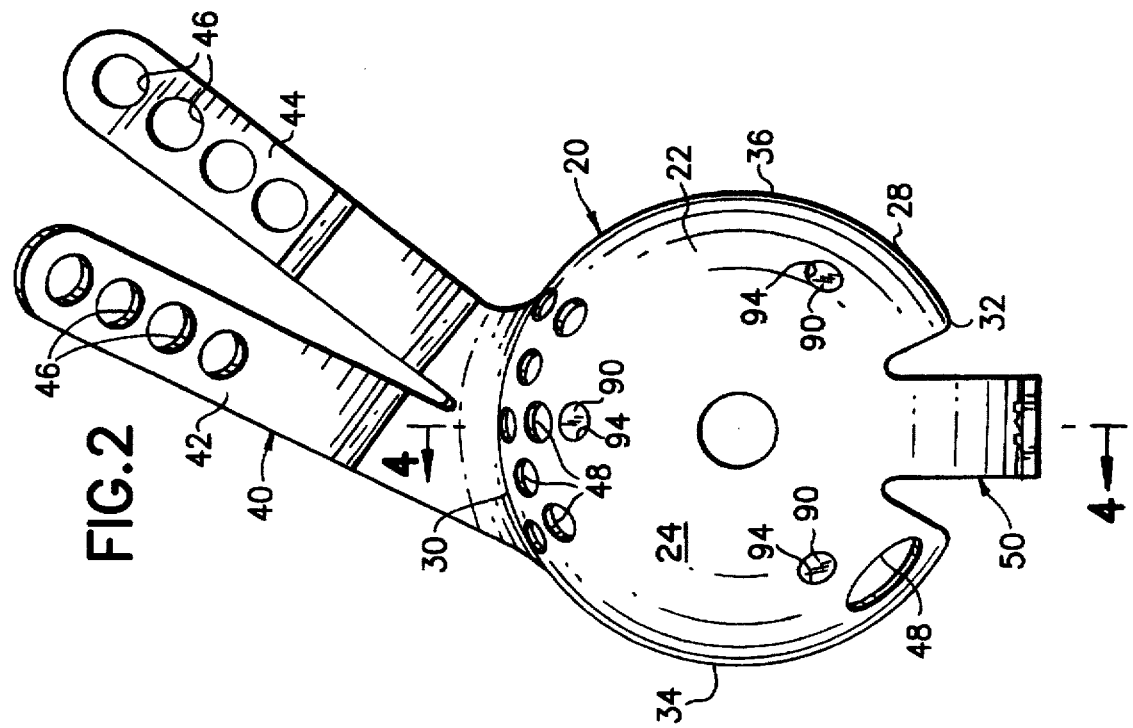
FIG. 2 is a plan view of the acetabular shell.

Turning now to FIGS. 2 and 3, acetabular shell 20 includes a domed portion 22 having a convex outer surface 24 for engaging the acetabulum 15 of the pelvis 14, and a concave inner surface 26 (see FIG. 4) for reception of the bearing insert 18. A rim 28 is located between the outer surface 24 and the inner surface 26 and includes a superior segment 30, an inferior segment 32 longitudinally opposite the superior segment 30, a posterior segment 34, and an anterior segment 36 laterally opposite the posterior segment 34. An anchoring plate 40 is integral with the domed portion 22 adjacent the superior segment 30 of the rim 28 and is bifurcated so as to include branches 42 and 44, each branch 42 and 44 extending in a generally superior direction and having a plurality of bone screw holes 46 passing through the plate 40. Likewise, a plurality of bone screw holes 48 pass through the domed portion 22 of the acetabular shell 20. A securing hook 50 is integral with the domed portion 22 adjacent the inferior segment 32 of the rim 28 and has a generally U-shaped overall configuration including an inner leg 52 and an opposite outer leg 54.

Figure 4:
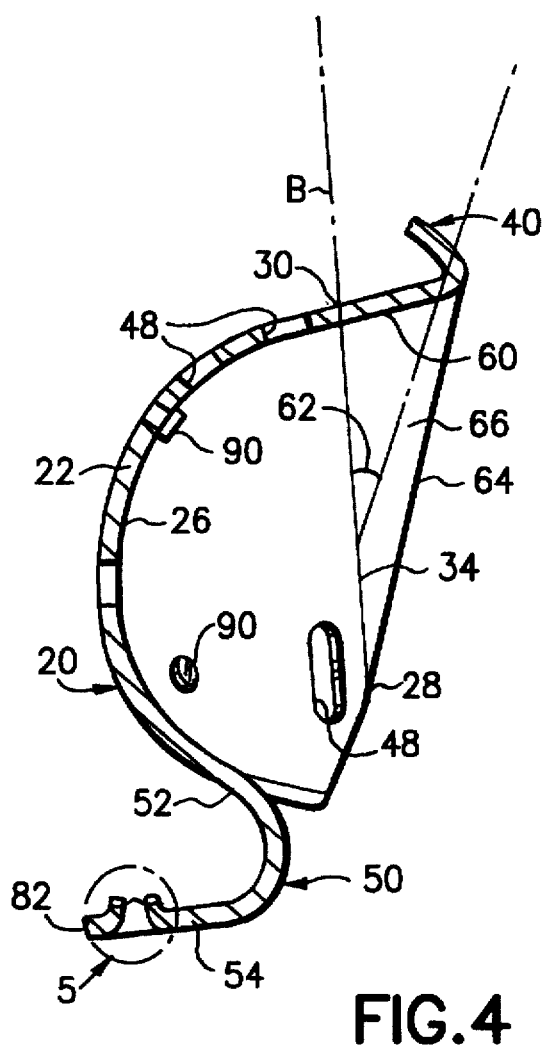
FIG. 4 is a fragmentary cross-sectional view taken along line 4—4 of FIG. 2.

As best seen in FIG. 4, the inner surface 26 of the domed portion 22 follows a generally spherical contour which extends to the rim 28, and the rim 28 is somewhat circular and is placed adjacent a generally equatorial location so that the inner surface 26 extends along the spherical contour up to, and preferably somewhat less than, an essentially hemispherical extent, which hemispherical extent is illustrated by the boundary B in FIGS. 1 and 4. In order to provide supplemental support for the bearing insert 18 in the posterior and superior directions, a supplemental support web 60 extends along the rim 28 from the posterior segment 34 to the plate 40 at the superior segment 30, where the web 60 projects beyond the boundary B. Preferably, the web 60 projects beyond the boundary B at the plate 40 for a distance indicated by angle 62, and the web 60 is tapered gradually along the edge 64 of the web 60 from the plate 40 toward the posterior segment 34 of the rim 28. The web 60 includes an interior surface 66 which extends from the spherical contour of the inner surface 26 along the web 60, in posterior and superior directions. Preferably, angle 62 is about 20° so that the web 60 projects beyond boundary B, adjacent the superior segment 30, for a distance of about 20° as measured along an extension of the generally spherical contour of inner surface 26 of the domed portion 22.

Implant is accomplished by first preparing the natural acetabulum 15 for the reception of the acetabular shell 20 and then seating the acetabular shell 20 within the acetabulum 15 of the pelvis 14. Just prior to seating of the acetabular shell 20 within the acetabulum 15, the branches 42 and 44 of the plate 40 are bent into configurations which will locate and conform the branches 42 and 44 to the best available bone of the pelvis 14. The domed portion 22 of the acetabular shell 20 then is seated within the prepared acetabulum 15 and bone screws, one of which is illustrated at 70, are inserted through selected bone screw holes 48 in the domed portion 22 so as to be secured within the best available bone. Further bone screws 72 are inserted through selected bone screw holes 46 in the plate 40 to extend into the best bone available at the branches 42 and 44. In this manner the acetabular shell 20 is secured in place in the pelvis 14, as seen in FIG. 1.

Figure 5:
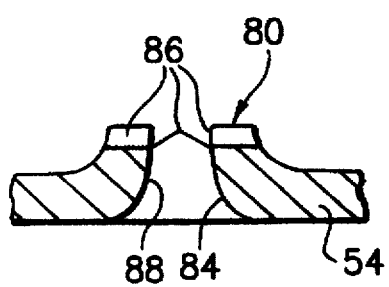
FIG. 5 is an enlarged fragmentary cross-sectional view of portion 5 of FIG. 2.

Upon seating the domed portion 22 within the pelvis 14, the securing hook 50 is placed around a corresponding portion 74 of the pelvis 14 and, just prior to insertion of the bone screws 70 and 72, and subsequent to seating of the domed portion 22 within the prepared acetabulum 15, the securing hook 50 is crimped, or deformed, by bending the outer leg 54 inwardly toward the inner leg 52 so that the securing hook 50 is deformed intraoperatively to grip the corresponding portion 74 of the pelvis 14 between the inner end outer legs 52 and 54 and hold the acetabular shell 20 in place for the subsequent insertion of the bone screws 70 and 72. In order to enhance the grip of the securing hook 50 upon the bone of the pelvis 14, a spur 80 is provided adjacent the tip 82 of the outer leg 54 of the hook 50. As best seen in FIG. 5, spur 80 includes a perforation 84 in the outer leg 54, and sharp projections 86 along the edge 88 of the perforation 84, the sharp projections 86 projecting from the outer leg 54 toward the inner leg 52 so as to be embedded in the bone of the pelvis 14 upon crimping of the hook 50, as set forth above.

Once the acetabular shell 20 is secured in place in the pelvis 14, the bearing member 18 is affixed within the acetabular shell 20. In the illustrated embodiment, the bearing member 18 is secured in place by a cemented affixation. To this end, the acetabular shell 20 is provided with a plurality of cement spacers 90 attached to the domed portion 22 and projecting inwardly from the inner surface 26 at spaced apart locations, as seen in FIG. 4, for establishing an essentially uniform and accurate cement mantle, as illustrated at 92 in FIG. 1, between the inner surface 26 of the domed portion 22 and the bearing insert 18. The cement spacers 90 preferably are constructed of polymethylmethacrylate (PMMA) and are secured within complementary apertures 94 in the domed portion 22. With the bearing insert 18 appropriately located and affixed within the acetabular shell 20, the supplemental support web 60 provides increased support for the bearing insert 18 in posterior and superior directions, as viewed in FIG. 1. In this manner, the prosthetic hip implant 10 enables increased support for the bearing insert 18 against forces encountered at the implant site during service.

Acetabular shell 20 preferably is constructed of a biocompatible metal, the preferred material being titanium. In the preferred construction, the plate 40, the securing hook 50 and the support web 60 are formed unitary with the domed portion 22 in a one-piece acetabular shell 20.

It will be seen that the present invention attains the objects and advantages summarized above, namely: Provides an acetabular shell of the type described and having a supplemental support configuration enabling increased support against forces encountered in the hip joint, without an increase in complexity in either the manufacture or in the procedure for implant of the acetabular shell; enables conformance of the acetabular shell to conditions encountered at the implant site for providing maximum effectiveness concomitant with those conditions; is adapted readily to accommodate a wider variety of conditions encountered at the implant site; provides for a more accurate and secure affixation of an acetabular bearing insert under a wider variety of conditions encountered at an implant site; facilitates the implant procedure with increased effectiveness in providing supplemental support for a bearing insert placed at the implant site; provides a relatively simple construction readily manufactured of an effective biocompatible material for increased economy, while attaining increased reliability over an extended service life.

It is to be understood that the above detailed description of preferred embodiments of the invention is provided by way of example only. Various details of design, construction and procedure may be modified without departing from the true spirit and scope of the invention, as set forth in the appended claims.

The embodiments of the invention in which an exclusive property or privilege is claimed are defined as follows:

1. An acetabular shell for implant at an acetabulum in a deficient pelvis to establish an effective acetabular site with increased support in posterior and superior directions for an acetabular bearing insert to be affixed in place in the acetabular shell for the reception of a femoral head of a femoral component of a prosthetic hip implant, the acetabular shell comprising:

a domed portion having a convex outer surface for engaging the acetabulum, a concave inner surface for reception of the bearing insert, the inner surface extending along a spherical contour up to a generally hemispherical extent, and a rim between the outer and inner surfaces, the rim being placed adjacent an equatorial location along the domed portion and including a superior segment, an inferior segment longitudinally opposite the superior segment, a posterior segment and an anterior segment laterally opposite the posterior segment;

an anchoring plate integral with the domed portion adjacent the superior segment of the rim; and a supplemental support web extending along the rim from the posterior segment to the anchoring plate at the superior segment, the support web projecting beyond the equatorial location for providing supplemental support for a bearing insert in the posterior and superior directions.

2. The invention of claim 1 wherein the supplemental support web projects beyond the equatorial location a distance of about 20° measured along an extension of the generally spherical contour of the inner surface of the domed portion adjacent the superior segment of the rim.

3. The invention of claim 1 wherein the supplemental support web tapers gradually from the plate toward the posterior segment of the rim.

4. The invention of claim 1 wherein the plate is bifurcated and includes two branches, each branch extending in a generally superior direction and including a plurality of screw holes.

5. The invention of claim 1 wherein the domed portion, the anchoring plate and the supplemental support web comprise a one-piece metal construction.

6. The invention of claim 1 including a plurality of cement spacers attached to the domed portion and projecting inwardly from the inner surface at spaced apart locations for establishing an essentially uniform and accurate cement mantle between the inner surface of the domed portion and a bearing insert upon securing the bearing insert in place in the acetabular shell by cemented affixation.

7. The invention of claim 1 including a securing hook integral with the domed portion adjacent the inferior segment of the rim, the securing hook having a generally U-shaped configuration including an inner leg and an opposite outer leg, the securing hook being selectively deformable intraoperatively to grip a corresponding portion of the pelvis between the inner and outer legs during implant of the acetabular shell.

8. The invention of claim 7 wherein the domed portion, the anchoring plate, the supplemental support web and the securing hook comprise a one-piece metal construction.

9. The invention of claim 7 including a spur on at least one of the inner and outer legs of the securing hook for increasing the grip between the one leg and the pelvis upon deforming the securing hook to grip the corresponding portion of the pelvis.

10. The invention of claim 9 wherein the spur is located on the outer leg.

11. The invention of claim 9 wherein the spur includes a perforation in the one leg, the perforation having edges, and sharp projections located along the edges of the perforation and directed toward the other of the inner and outer legs.

12. The invention of claim 11 wherein the spur is located on the outer leg.

13. A method for providing increased support against posterior and superior forces exerted upon an acetabular bearing insert implanted at an acetabulum in a deficient pelvis for the reception of a femoral head of a femoral component of a prosthetic hip implant, the method comprising:

placing an acetabular shell at the acetabulum of the pelvis, the acetabular shell including a domed portion having a convex outer surface for engaging the natural acetabulum, a concave inner surface for reception of the bearing insert, the inner surface extending along a spherical contour up to a generally hemispherical extent, and a rim between the outer and inner surfaces, the rim being placed adjacent an equatorial location along the domed portion and including a superior segment, an inferior segment longitudinally opposite the superior segment, a posterior segment and an anterior segment laterally opposite the posterior segment;

securing the domed portion in the pelvis by anchoring an anchoring plate in the pelvis, the anchoring plate being integral with the domed portion adjacent the superior segment of the rim; and locating a supplemental support web of the domed portion for supplemental support of the bearing insert in the posterior and superior directions, the supplemental support web extending along the rim from the posterior segment to the plate at the superior segment and projecting beyond the equatorial location for providing the supplemental support for a bearing insert in posterior and superior directions.

14. The invention of claim 13 wherein the acetabular shell includes a securing hook integral with the domed portion adjacent the inferior segment of the rim, the securing hook having a generally U-shaped configuration including an inner leg and an outer leg, and deforming the securing hook intraoperatively to grip a corresponding portion of the pelvis between the inner and outer legs during implant of the acetabular shell.

15. The invention of claim 14 wherein the securing hook includes a spur on at least one of the inner and outer legs and the step of deforming the securing hook embeds the spur within the pelvis.

16. The invention of claim 15 wherein the spur is located on the outer leg and the step of deforming the securing hook includes bending the outer leg toward the inner leg.

* * * * *